United States Patent [19]
Heiber et al.

[11] Patent Number: 5,212,199
[45] Date of Patent: May 18, 1993

[54] SORBITAN ESTERS AS SKIN PERMEATION ENHANCERS

[75] Inventors: Sonia Heiber, Salt Lake City; Dinesh Patel, Murray; Charles D. Ebert, Salt Lake City, all of Utah

[73] Assignee: Theratech, Inc., Salt Lake City, Utah

[21] Appl. No.: 871,643

[22] Filed: Apr. 21, 1992

Related U.S. Application Data

[63] Continuation of Ser. No. 702,043, May 17, 1991, Pat. No. 5,122,383.

[51] Int. Cl.$^5$ .............................................. A01N 45/38
[52] U.S. Cl. ..................................... 514/415; 514/777; 514/946; 514/947; 424/449; 536/119
[58] Field of Search ............... 424/449, 445, 443, 447; 514/415, 777, 946, 947

[56] References Cited

U.S. PATENT DOCUMENTS

4,685,911  8/1987  Konno et al. ..................... 424/448
5,122,383  6/1992  Heiber et al. ..................... 424/448

Primary Examiner—Thurman K. Page
Assistant Examiner—Leon R. Horne
Attorney, Agent, or Firm—Morrison & Foerster

[57] ABSTRACT

Skin permeation enhancer compositions are provided which increase the permeability of skin to transdermally administered pharmacologically active agents. The compositions contain a sorbitan ester in addition to the selected pharmacologically active agent, and may also contain a $C_1$–$C_4$ aliphatic alcohol. Methods and transdermal drug delivery systems for using the compositions are also provided.

21 Claims, 1 Drawing Sheet

SORBITAN ESTERS AS SKIN PERMEATION ENHANCERS

This application is a continuation, of application Ser. No. 07/702,043 filed, May 17, 1991 now U.S. Pat. No. 5,122,383.

TECHNICAL FIELD

The present invention relates generally to the transdermal administration of pharmacologically active agents, and more particularly relates to methods and compositions for enhancing the permeability of the skin to such agents.

BACKGROUND

The delivery of drugs through the skin provides many advantages; primarily, such a means of delivery is a comfortable, convenient and noninvasive way of administering drugs. The variable rate of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs. The stratum corneum is a thin layer of dense, highly keratinized cells approximately 10-15 microns thick over most of the body.

In order to increase skin permeability, and in particular to increase the permeability of the stratum corneum (i.e., so as to achieve enhanced penetration, through the skin, of the drug to be administered transdermally), the skin may be pretreated with a penetration enhancing agent (or "permeation enhancer", as sometimes referred to herein) prior to application of a drug. Alternatively, and preferably, a drug and a permeation enhancer are delivered concurrently.

The present invention is directed to a novel composition for enhancing the penetration of pharmacologically active agents through skin, the composition based on a sorbitan ester as will be described herein. The composition may or may not contain an aliphatic alcohol as an additional component. The sorbitan ester compositions of the invention have been found by the inventors herein to be particularly effective in enhancing the penetration of pharmaceutically active agents through skin.

While there are a number of patents and publications available which relate to the transdermal administration of drugs and to skin permeation enhancer compositions, applicants are unaware of any art which suggests that sorbitan esters are useful as permeation enhancers in the absence of additional permeation enhancing compounds or which describes the sorbitan ester/aliphatic alcohol compositions as described and claimed herein.

CITATION OF ART

The following references relate to one or more aspects of the present invention.

Skin permeation enhancers, generally: Various compounds for enhancing the permeability of skin are known in the art. U.S. Pat. Nos. 4,006,218, 3,551,554 and 3,472,931, for example, respectively describe the use of dimethylsulfoxide (DMSO), dimethyl formamide (DMF) and N,N-dimethylacetamide (DMA) to enhance the absorption of pharmacologically active agents through the stratum corneum. Other compounds which have been used to enhance skin permeability include: decylmethylsulfoxide ($C_{10}MSO$); diethylene glycol monoethyl ether; polyethylene glycol monolaurate (PEGML; see, e.g., U.S. Pat. No. 4,568,343); glycerol monolaurate (U.S. Pat. No. 4,746,515); propylene glycol monolaurate; ethanol (e.g., as in U.S. Pat. No. 4,379,454); eucalyptol (U.S. Pat. No. 4,440,777); lecithin (U.S. Pat. No. 4,783,450); the 1-substituted azacycloheptan-2-ones, particularly 1-n-dodecylcyclazacycloheptan-2-one (available under the trademark Azone® from Nelson Research & Development Co., Irvine, Calif.; see U.S. Pat. Nos. 3,989,816, 4,316,893, 4,405,616 and 4,557,934); propylene glycol in combination with a fatty acid such as linoleic acid (European Patent Publication No. 261429); "cell envelope disordering compounds" such as methyl laurate or oleic acid in combination with N-(hydroxyethyl) pyrrolidone (U.S. Pat. No. 4,537,776); $C_3$-$C_4$ diols (U.S. Pat. No. 4,552,872, European Patent Application Publication No. 043738); or a binary system of oleic acid, oleins or oleyl alcohol in combination with a lower alcohol (U.S. Pat. No. 4,863,970).

Sorbitan analogs as permeation enhancers, specifically: T. Ogiso et al., *J. Pharmacobio-Dyn.*, 9:517-525 (1986), presents studies on percutaneous absorption in vivo and the penetration in vitro of indomethacin. Sorbitan monooleate was tested as a permeation enhancer in combination with a dimethyl sulfoxide (DMSO) gel and was found to have no enhancing effect. T. Ogiso et al., *J. Pharm. Sci.*, 78(4):319-323 (1989), describes the combined use of laurocapram and sorbitan monooleate in a permeation enhancer composition also containing a DMSO gel, for the transdermal administration of indomethacin. W.-W. Shen et al., *J. pharm. Sci.*, 65(12):1780-1783 (1986), describes the effect of various nonionic surfactants, including sorbitan monopalmitate and sorbitan trioleate, on the percutaneous absorption of salicylic acid. As with the latter two references, the sorbitan esters are used in conjunction with DMSO. U.S. Pat. No. 4,637,930 to Konno et al. describes a transdermal formulation for the administration of nicardipine hydrochloride which contains a mixed liquid composed of urea and an additional compound which may be a sorbitan "middle chain" (6-12 carbon atom) fatty acid ester.

SUMMARY OF THE INVENTION

Accordingly, it is a primary object of the invention to provide a method for enhancing the rate of penetration of a pharmacologically active agent through the skin.

It is another object of the invention to provide such a method which involves applying to a selected area of intact skin a therapeutically effective amount of the selected pharmacologically active agent in combination with a permeation enhancer composition containing a sorbitan ester.

It is still another object of the invention to provide such a method wherein the permeation enhancer composition consists essentially of: (1) a sorbitan ester; or (2) a sorbitan ester in combination with an aliphatic alcohol as will be described in detail herein.

It is a further object of the invention to provide a skin permeation enhancer composition comprising the pharmacologically active agent and a permeation enhancer composition which consists essentially of: (1) a sorbitan ester; or (2) a sorbitan ester in combination with an aliphatic alcohol.

It is still a further object of the invention to provide a transdermal system in the form of a laminated composite designed to adhere to the skin. The composite contains, in addition to the selected pharmacologically active agent to be administered, a permeation enhancer composition containing a sorbitan ester, and, optionally, an aliphatic alcohol.

Additional objects, advantages and novel features of the invention will be set forth in part in the description which follows, and in part will become apparent to those skilled in the art upon examination of the following, or may be learned by practice of the invention.

In one aspect, the invention is a method for administering a pharmacologically active agent transdermally so as to achieve relatively high transdermal fluxes, by administering, through a predetermined area of intact skin and for a predetermined period of time, (1) the agent, and (2) a permeation enhancer consisting essentially of a sorbitan ester, or a in combination with a $C_1$–$C_4$ aliphatic alcohol. In a preferred embodiment, the skin permeation enhancer and the drug are administered in a single composition. As the clearance rate of many drugs from the body is quite high, it is generally preferred that administration be substantially continuous throughout the time period chosen for patch application.

In another aspect of the invention, a composition of matter is provided that is useful for the delivery of a pharmacologically active agent through the skin, comprising:

(a) a therapeutically effective amount of the pharmacologically active agent to be administered; and (b) an amount of a permeation enhancer composition effective to enhance the penetration of the pharmacologically active agent through the skin, wherein the enhancer consists essentially of a sorbitan ester or a sorbitan ester combined with a $C_1$–$C_4$ aliphatic alcohol.

In still another aspect of the invention, a therapeutic system is provided for administering a drug transdermally, at relatively high fluxes as noted above, in the form of a skin patch. The skin patch is preferably in the form of a matrix-type laminated composite containing an upper backing layer that is substantially impermeable to the drug, and at least one drug/enhancer reservoir, one of which forms the basal surface of the device and is designed to adhere to the skin during use. The reservoir is a matrix which contains both the drug and a permeation enhancer as described above. Such a laminated composite preferably includes a strippable protective release liner laminated to the basal surface of the drug reservoir. The release liner is a disposable element designed to protect the exposed reservoir surface prior to use. In an alternative embodiment, a transdermal therapeutic system is provided in the form of a liquid reservoir-type laminated composite, e.g., as described in commonly assigned U.S. Pat. No. 4,849,224 to Chang et al., the disclosure of which is incorporated by reference herein.

Detailed Description of the Invention

Figure 2:
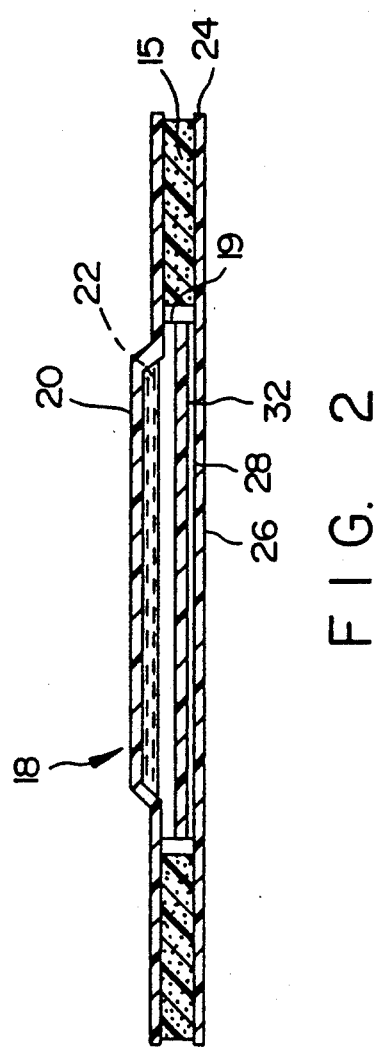
FIG. 2 is a schematic sectional view through a laminated liquid reservoir-type transdermal system of the invention.

Before describing the present compositions, systems and methods of the invention in detail, it is to be understood that this invention is not limited to the particular drugs, sorbitan esters, aliphatic alcohols, or laminate materials described herein as such may, of course, vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the content clearly dictates otherwise. Thus, for example, reference to a laminated structure containing "a drug" includes a mixture of two or more drugs, reference to "an adhesive" includes reference to one or more of such adhesives, and reference to "a sorbitan ester" includes reference to a mixture of two or more sorbitan esters.

In describing and claiming the present invention, the following terminology will be used in accordance with the definitions set out below.

"Penetration enhancement" or "permeation enhancement" as used herein relates to an increase in the permeability of skin to a pharmacologically active agent, i.e., so as to increase the rate at which the agent permeates into and through the skin. A "permeation enhancer" is a material which achieves such permeation enhancement, and a "penetration enhancing amount" of an enhancer as used herein means an amount effective to enhance skin penetration of a selected agent to a desired degree.

By "transdermal" drug delivery, applicant is using the term in its conventional sense, i.e., to indicate delivery of a drug by passage through the skin and into the blood stream. By "transmucosal" drug delivery, applicant intends delivery of a drug by passage of a drug through the mucosal tissue into the blood stream. "Topical" drug delivery is used to mean local administration of a topical drug as in, for example, the treatment of various skin disorders. These terms will sometimes be used interchangeably herein, i.e., aspects of the invention which are described in the context of "transdermal" drug delivery, unless otherwise specified, can apply to transmucosal or topical delivery as well. That is, the compositions, systems, and methods of the invention, unless explicitly stated otherwise, should be presumed to be equally applicable with any one of these three modes of drug delivery.

The term "drug" or "pharmacologically active agent" as used herein is intended to mean a compound or composition of matter which, when administered to an organism (human or animal) induces a desired pharmacologic and/or physiologic effect by local and/or systemic action. In general, the terms include the therapeutic or prophylactic agents in all major therapeutic/prophylactic areas of medicine. Examples of drugs useful in conjunction with the present invention include: anti-infectives such as antibiotics and antiviral agents;

analgesics and analgesic combinations; anorexics; antihelminthics; antiarthritics; antiasthmatic agents; anticholinergic agents; anticonvulsants; antidepressants; antidiabetic agents; antidiarrheals; antihistamines; antiinflammatory agents, antimigraine preparations; antimotion sickness drugs; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; steroids; hypnotics; immunosuppressives; muscle relaxants; parasympatholytics; psychostimulants; sedatives; and tranquilizers. For purposes of the aforementioned definition, "drugs" as used herein also include locally administered topical medicaments such as antibacterial agents, antifungals, antimicrobials, cutaneous growth enhancers, antipsoriatics, anti-acne medicaments, and the like.

"Carriers" or "vehicles" as used herein refer to carrier materials without pharmacological activity which are suitable for administration in conjunction with the presently disclosed and claimed compositions, and include any such carrier or vehicle materials known in the art, e.g., any liquid, gel, solvent, liquid diluent, solubilizer, or the like. The carriers and vehicles suitable herein are "pharmaceutically acceptable" in that they are nontoxic, do not interfere with drug delivery, and are not for any other reasons biologically or otherwise undesirable. Examples of specific suitable carriers and vehicles for use herein include water, mineral oil, silicone, inorganic gels, aqueous emulsions, liquid sugars, waxes, petroleum jelly, and a variety of other oils and polymeric materials.

By a "therapeutically effective" amount of a drug or pharmacologically active agent is meant a nontoxic but sufficient amount of the drug or agent to provide the desired therapeutic effect.

The invention is thus in one embodiment a method for enhancing the rate of penetration of a pharmacologically active agent through the skin, wherein the method involves co-administration of the agent through a predetermined area of intact skin, and for a predetermined period of time, the selected agent and a permeation enhancer consisting essentially of a sorbitan ester or a sorbitan ester in combination with a $C_1$-$C_4$ aliphatic alcohol. The sorbitan esters which are useful in conjunction with the present invention have the structure

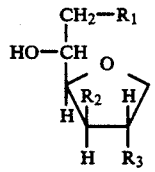

wherein the substituent $R_1$ has the structure —O(-CO)R′, where R′ is selected from the group consisting of saturated, mono-unsaturated, di-unsaturated and tri-unsaturated aliphatic hydrocarbon substituents of 7 to 21 carbon atoms, preferably 11 to 21 carbon atoms, and may be substituted with 1 to 3 hydroxyl groups. The substituents $R_2$ and $R_3$ may be the same or different and are selected from the group consisting of hydroxyl and —O(CO)R′ as defined above. $R_1$, $R_2$ and $R_3$, may be, for example, lauryl, myristyl, palmityl, stearyl, palmitoleyl, oleyl, linoleyl, linolenyl, or ricinoleyl esters, or the like. Exemplary sorbitan esters are longchain sorbitan monoesters, wherein $R_1$ is as defined above, R′ is hydrocarbon of 11 to 21 carbon atoms, and $R_2$ and $R_3$ are both hydroxyl. Particularly preferred compounds within the class of sorbitan monoesters are sorbitan monooleate and sorbitan monolaurate.

In addition to a sorbitan ester, the permeation enhancer composition of the invention may also include a $C_1$-$C_4$ aliphatic alcohol component. Examples of suitable alcohols within this class include ethanol, n-propanol, isopropanol, t-butanol, and mixtures thereof.

The method of delivery of the present compositions may vary, but necessarily involves application of drug and enhancer to a selected intact surface of the skin or other tissue for a period of time sufficient to provide the desired blood level of drug. The method preferably involves administration of drug and enhancer simultaneously, in a single composition, i.e., as an ointment, gel, cream, or the like, or may involve use of a drug delivery device as taught, for example, in U.S. Pat. Nos. 4,849,224, 4,983,395, 4,568,343, 3,797,494 or 3,742,951.

When the drug to be administered and the permeation enhancer as described above are applied in the form of an ointment, gel, cream or the like, the amount of drug contained within the composition will depend on a variety of factors, including the desired rate of delivery, the desired dosage, the disease to be treated, the nature and activity of the drug, the desired effect, possible adverse reactions, the ability and speed of the drug selected to reach its intended target, and other factors within the particular knowledge of the patient and the physician. The amount of enhancer will typically be in the range of 0.1 wt. % to 40 wt. % relative to the total composition, more preferably on the order of about 2.5 wt. % to 15 wt. %. The composition may, in addition to drug and enhancer, include one or more selected carriers or excipients, and/or various agents and ingredients commonly employed in dermatological ointments and lotions. For example, fragrances, opacifiers, preservatives, antioxidants, gelling agents, perfumes, thickening agents, stabilizers, surfactants, emollients, coloring agents, and the like may be present so long as they are pharmaceutically acceptable and compatible with the drug and enhancer.

Figure 1:
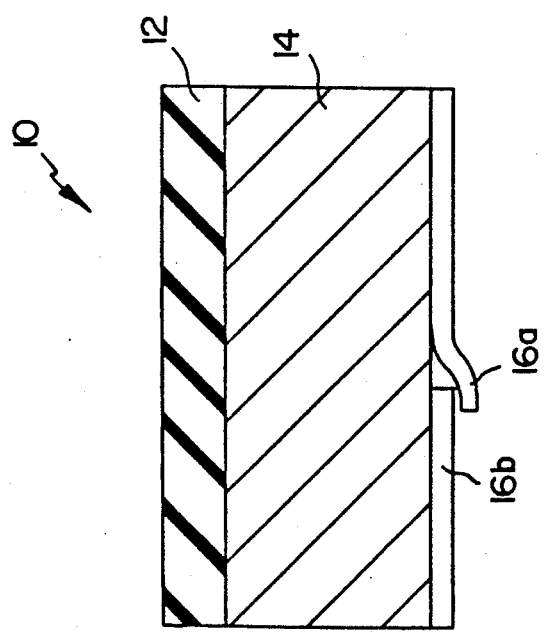
FIG. 1 is a schematic sectional view through a laminated matrix-type transdermal system of the invention.

A transdermal delivery system for the administration of a drug can be constructed with the drug/enhancer composition described hereinabove. Preferred transdermal drug delivery systems for use herein are laminated composites which contain one or more drug/permeation enhancer reservoirs, a backing layer and, optionally, one or more additional layers (e.g., additional drug and/or enhancer reservoirs) as those skilled in the art of transdermal drug delivery will readily appreciate. FIG. 1 depicts an exemplary system, generally designated 10, that when applied to skin administers a selected pharmacologically active agent as outlined above. System 10 is a laminated composite in which the top layer 12 is a backing layer, its face forming the top surface of the composite. The drug reservoir, containing drug, enhancer as described herein, and optional carriers or vehicles, is shown at 14, immediately below and adjacent to the backing layer. Prior to use, the laminate also includes a strippable protective release liner. In a preferred embodiment, as described in copending commonly assigned Ser. No. 07/625,906, filed Dec. 10, 1990, and entitled "Method and Systems for Administering Nitroglycerin Transdermally at Enhanced Transdermal Fluxes," the release liner is in the form of two sheets 16a and 16b, the first sheet 16a partially overlapping the second sheet 16b. Additional structural layers and/or additional drug/enhancer reservoirs may also be present.

The drug reservoir is preferably comprised of a contact adhesive which is a pressure-sensitive adhesive suitable for long-term skin contact. It must also be physically and chemically compatible with the drug and enhancer employed, and with any carriers or vehicles incorporated into the drug/enhancer composition. Further, the adhesive selected for use as the reservoir layer must be such that the drug and enhancer are at least somewhat soluble in the adhesive. The drug reservoir will generally be in the range of about 2 to 4 mils in thickness. Suitable adhesives for use as the drug reservoir include polysiloxanes, polyacrylates, polyurethanes, tacky rubbers such as polyisobutylene, and the like. Particularly preferred contact adhesives for use as the drug reservoir herein are cross-linked acrylates (e.g., the Durotak ® adhesives, available from National Starch & Chemical Co., New York, N.Y., or the Gelvae adhesives, available from Monsanto Co., St. Louis, Mo.).

The backing layer, which is, as shown, adhered to the drug reservoir and serves as the upper layer of the device during use, functions as the primary structural element of the device. The backing layer is made of a sheet or film of a preferably flexible elastomeric material that is substantially impermeable to the drug/enhancer composition. The layer will typically be on the order of 1.0 to about 4.0 mils in thickness, and is preferably of a material that permits the device to follow the contours of the skin, such that it may be worn comfortably on any skin area, e.g., at joints or other points of flexure. In this way, in response to normal mechanical strain, there is little or no likelihood of the device disengaging from the skin due to differences in the flexibility or resiliency of the skin and the device. Examples of polymers useful for the backing layer herein are polyethylene, polypropylene, polyesters, polyurethanes, polyethylene vinyl acetate, polyvinylidene chloride, block copolymers such as PEBAX, and the like. The backing layer may also comprise laminates of one or more of the foregoing polymers.

The release liner is a disposable element which serves only to protect the device prior to application. Typically, the release liner is formed from a material impermeable to the drug, vehicle, and adhesive, and which is easily stripped from the contact adhesive that serves as the drug reservoir layer. Preferred release liners for use herein are those which are generally suitable for use in conjunction with pressure-sensitive adhesives. Silanized polyester films are presently preferred.

In a preferred embodiment, as noted above, a two-part release liner is used, wherein a first strippable protective sheet (shown as 16a in FIG. 1) partially overlaps a second strippable protective sheet 16b, such that the area of overlap gives rise to a tab which extends from the basal surface of the laminate, enabling ready removal of the strippable sheets from the reservoir layer.

The preferred laminated composites of the invention are as shown in FIG. 1, having a backing layer, a drug reservoir, and a two-piece release liner; the drug reservoir contains a drug/enhancer composition as described above, with the quantity of the drug therein, and with the remainder of the drug reservoir comprised of adhesive and optional carriers, vehicles or the like. If the drug is a hydrophobic material such as a steroid, it is preferred that the quantity of drug contained within the reservoir is at "subsaturation" as described in detail in applicants' copending, commonly assigned U.S. application Ser. No. 07/626,685, filed Dec. 11, 1990, the disclosure of which is hereby incorporated by reference in its entirety. To use these laminated composites, one is applied directly to the skin of a patient, to release the drug/enhancer composition to the skin, allowing the drug to permeate into the circulation. The adhesive layer which serves as the drug reservoir should be in firm contact with the skin.

In general, such devices are fabricated using methods standard in the art, e.g., solvent-evaporation film casting in which all components of the drug/enhancer composition are admixed with the adhesive which will serve as the drug reservoir, and cast onto a substrate which is either the backing layer or release liner. Other layers are then laminated to this initial structure.

In an alternative embodiment, laminated composites containing drug in a liquid reservoir, as described in U.S. Pat. No. 4,849,224, may be used. As described in that patent, the disclosure of which is incorporated by reference herein, such devices shown generally at 18 in FIG. 2 are comprised of an uppermost layer of a heat-sealable backing film 20 having an inverted, cup-shaped recess that serves the reservoir 22 for the drug-enhancer formulation. The underside of the outer edge of the backing film carries a ring-shaped layer 24 of a pressure-sensitive adhesive peripheral to the reservoir. Underlying the reservoir, just inward of the peripheral ring of adhesive, is a membrane layer 26 that is permeable to the drug-enhancer formulation. A peel sealable inner liner 28 underlies membrane 26 and portions of backing film 20. A peel-sealable release liner 30 covers the entire underside of the assembly and forms the basal surface of the device. Device 18 has a heat seal 32 between the membrane and backing film and a peelable (impermanent) heat seal 34 between the backing film and the inner liner 28. An alternative liquid reservoir-type device which may be used in conjunction with the present compositions is described in U.S. Pat. No. 4,983,395, also incorporated by reference herein.

Preferred daily dosages obtained with the present methods and systems will, similarly, vary with the drug administered. The targeted daily dosage will depend on the individual being treated, the indication addressed, the length of time the individual has been on the drug, and the like.

EXPERIMENTAL

The following examples are put forth so as to provide those with ordinary skill in the art with a complete disclosure and description of how to formulate compositions and systems of the invention, and are not intended to limit the scope of what the inventors regard as their invention. Efforts have been made to ensure accuracy with respect to numbers used (e.g., amounts, temperatures, etc.), but some experimental errors and deviations should be allowed for. Unless indicated otherwise, parts are parts by weight, temperatures are in degrees Centigrade, and pressure is at or near atmospheric.

Estradiol, norethindrone acetate, progesterone and pindolol were obtained from Sigma Chemical Co., St. Louis, Mo. Polyacrylate adhesive solutions were obtained from National Starch & Chemical Co., New Jersey (Durotak® 80-1194, 80-1054, 80-1070) and from Monsanto Corporation (Gelva® 737). Sorbitan monooleate, sorbitan monolaurate and sorbitan trioleate were all obtained from ICI Americas. Ethanol (USP 95%) was obtained from Fisher Scientific.

Adhesive laminates were formulated by mixing the selected polyacrylate solutions with drug and/or enhancer, followed by evaporation of solvent. The concentrated solution was cast onto the silanized surface of a polyester release liner (Release Technologies, 2-EST-A-S242M), using a 10 mil gap Gardner knife. The cast adhesive was then dried at 80° C. for 15 minutes in a convection oven to yield a final 0.050 inch thick adhesive coating. A 0.0075 inch thick low density polyethylene film (Schoeller Technical Paper Co., New York) was then laminated onto the dried adhesive surface to produce a three-layer transdermal matrix system construction.

The in vitro skin flux of the particular drugs tested was evaluated across human cadaver skin as described by Merrit and Cooper (*J. Controlled Release* (1984) 1:161) using a high-performance liquid chromatography (HPLC) assay. For these studies the release liner was removed from a previously cut section of the above transdermal matrix construction. The adhesive matrix was then positioned onto the stratum corneum surface of heat separated human epidermis and the skin, with the adhering transdermal system, was then immediately mounted onto the diffusion cell. The steady state flux ($\mu g/cm^2/hr$) of drug was determined by linear regression analysis of the cumulative amount of drug permeating ($\mu g/cm^2$) across the skin as a function of the time (hr).

EXAMPLE 1

The aforementioned procedure was used to evaluate the effect of increasing sorbitan ester levels on estradiol flux from acrylic adhesives. The sorbitan ester used was sorbitan monolaurate ("SML"); the acrylic adhesive used Was Durotak® 80-1194 ("1194").

Results are set forth in Table I. As may be seen, the flux obtained was found to increase with increasing quantities of sorbitan monolaurate.

TABLE I

Effect of Increasing Sorbitan Monolaurate Levels on Estradiol Flux from an Acrylic Adhesive

| Enhancer System | Estradiol Conc. (mg/ml) | Flux ($\mu g/cm^2/hr$) |
|---|---|---|
| None | 2 wt. % | 0.26 ± 0.05 |
| 5 wt. % SML | 2 wt. % | 0.34 ± 0.09 |
| 10 wt. % SML | 2 wt. % | 0.43 ± 0.08 |

EXAMPLE 2

The procedure of Example 1 was followed to evaluate the effect of sorbitan monooleate ("SMO") and sorbitan monolaurate on estradiol flux from three different acrylic adhesive matrices, Durotak® 80-1194 ("1194"), Durotak® 80-1054 ("1054") and Durotak® 80-1070 ("1070"). All systems tested contained 4 wt. % estradiol. As may be deduced from the results set forth in the following table, the two sorbitan esters were found to significantly increase flux in all three types of adhesive matrices.

TABLE II

Effect of Sorbitan Esters on Estradiol Flux From Three Different Acrylic Adhesive Matrices

| Formulation | Flux ($\mu g/cm^2/hr$) |
|---|---|
| 1194 | 0.38 ± 0.36 |
| 1194/15% SMO | 1.69 ± 0.58 |
| 1194/15% SML | 0.96 ± 0.47 |
| 1054 | 0.55 ± 0.12 |
| 1054/15% SMO | 0.95 ± 0.40 |
| 1054/15% SML | 1.07 ± 0.07 |
| 1070 | 0.41 ± 0.07 |
| 1070/15% SMO | 0.68 ± 0.13 |
| 1070/15% SMO | 0.99 ± 0.31 |

EXAMPLE 3

The procedure above was followed to prepare additional acrylic adhesive matrices containing estadiol (both with and without a sorbitan ester), so as to evaluate the effect of Drug loading on estradiol flux. The acrylic adhesive used was Durotak® 80-1070 ("1070"), and the sorbitan ester used was sorbitan monooleate (present at subsaturation in all systems tested). Results are set forth in Table III. Sorbitan monooleate was found to increase estradiol flux in both of the systems tested.

TABLE III

Effect of Drug Loading on Estradiol Flux from an Acrylic Adhesive Matrix With and Without Sorbitan Monooleate

| Formulation | Skin 1 ($\mu g/cm^2/hr$) | Skin 2 ($\mu g/cm^2/hr$) |
|---|---|---|
| 1 wt. % estradiol, no enhancer | 0.22 ± 0.08 | 0.34 ± 0.03 |
| 2 wt. % estradiol, no enhancer | 0.56 ± 0.08 | 0.72 ± 0.09 |
| 1 wt. % estradiol, 5 wt. % SMO | 0.43 ± 0.18 | 0.55 ± 0.07 |
| 2 wt. % estradiol, 5 wt. % SMO | 1.00 ± 0.16 | 0.98 ± 0.08 |

EXAMPLE 4

The procedure above was followed to prepare additional acrylic adhesive matrices (Duortak® 80-1194) containing estradiol. One system was prepared with sorbitan trioleate ("STO") as an enhancer, and a second system was prepared without sorbitan trioleate. The flux obtained with the sorbitan trioleate system was approximately 52% higher than that obtained with the control system. Results are set forth in Table IV.

TABLE IV

Effect of Sorbitan Trioleate on Estradiol Flux ($\mu g/cm^2/hr$) from an Acrylic Adhesive Matrix

| Formulation | Flux ($\mu g/cm^2/hr$) |
|---|---|
| 4 wt. % estradiol, no enhancer | 0.78 ± 0.13 |
| 4 wt. % estradiol, 10 wt. % STO | 1.19 ± 0.13 |

EXAMPLE 5

The procedure above was followed to prepare acrylic adhesive matrices (Durotak® 80-1194 and 80-1054) containing 10 wt. % norethindrone acetate. Systems were prepared with and without 15 wt. % sorbitan ester; both sorbitan monooleate and sorbitan monolaurate were tested, as shown in Table V. As may be concluded from the results summarized in the table, both sorbitan monooleate and sorbitan monolaurate significantly increased norethindrone acetate flux in both adhesive systems.

TABLE V

Effects of Sorbitan Esters on Norethindrone Acetate Flux from Acrylic Adhesives Matrices

| Formulation | Skin 1 (μg/cm²/hr) | Skin 2 (μg/cm²/hr) |
| --- | --- | --- |
| 1194/no enhancer | 0.21 ± 0.02 | 0.24 ± 0.02 |
| 1194/15% SMO | 0.38 ± 0.20 | 0.31 ± 0.01 |
| 1194/15% SML | 0.43 ± 0.09 | 0.60 ± 0.03 |
| 1054/no enhancer | — | 0.27 ± 0.06 |
| 1054/15% SMO | — | 0.40 ± 0.11 |
| 1054/15% SML | — | 0.54 ± 0.06 |

EXAMPLE 6

The procedure above was followed to prepare acrylic adhesive matrices using Gelva® 737 ("737") containing 5 wt. % pindolol. Systems were prepared with 15 wt. % sorbitan monooleate, 15 wt. % sorbitan monolaurate, and 15 wt. % sorbitan trioleate, and compared with a system not containing any sorbitan ester. Again, the flux of drug was found to be significantly higher for all of the systems formulated with the sorbitan esters, relative to the control. Results are set forth in Table VI.

TABLE VI

Effects of Sorbitan Esters on Pindolol Flux from Acrylic Adhesive Matrices

| Formulation | Flux (μg/cm²/hr) |
| --- | --- |
| 737/no enhancer | 0.23 ± 0.05 |
| 737/15% SMO | 0.55 |
| 737/15% SML | 0.75 ± 0.26 |
| 737/15% STO | 0.55 ± 0.19 |

EXAMPLE 7

Flux of progesterone from ethanolic solutions of the drug was evaluated as follows.

Ethanol/water/glycerin/sorbitan ester ointments were prepared as summarized in Table VII, and the flux of the drug therefrom evaluated.

TABLLE VII

Progesterone Flux From Ethanolic Solutions Containing Sorbitan Ester

| EtOH | H2O | Glycerin | SMO | SML | Flux μg/cm²/hr |
| --- | --- | --- | --- | --- | --- |
| — | 88 | 10 | 2 | — | 0.61 ± 0.03 |
| — | 88 | 10 | — | 2 | 1.21 ± 0.19 |
| 60 | 30 | 10 | — | — | 6.29 ± 0.77 |
| 60 | 28 | 10 | 2 | — | 13.04 ± 1.52 |
| 60 | 28 | 10 | — | 2 | 10.33 ± 4.02 |

The data summarized in Table 7 clearly demonstrates a synergistic enhancement for progesterone when ethanol is combined with sorbitan monolaurate or sorbitan monooleate.

We claim:

1. A method for enhancing the rate of penetration of a pharmacologically active agent through the skin, comprising applying to a selected area of intact skin: (a) a therapeutically effective amount of the pharmacologically active agent; and (b) a permeation enhancer consisting essentially of a sorbitan ester having the structural formula

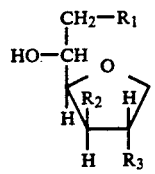

wherein $R_1$ has the formula —O(CO)R', R' is selected from the group consisting of saturated, mono-unsaturated, di-unsaturated, or tri-unsaturated aliphatic hydrocarbon substituents of 7 to 21 carbon atoms optionally containing 1 to 3 hydroxyl groups, and $R_2$ and $R_3$ are independently selected from the group consisting of hydroxyl and —O(CO)R'.

2. The method of claim 1 wherein R' is selected from the group consisting of saturated, mono-unsaturated, di-unsaturated, or tri-unsaturated aliphatic hydrocarbon substituents of 11-21 carbon atoms optionally containing 1-3 hydroxyl groups, and $R_2$ and $R_3$ are both hydroxyl.

3. The method of claim 2 wherein the sorbitan ester is selected from the group consisting of sorbitan monooleate, sorbitan monolaurate, and mixtures thereof.

4. The method of claim 1 wherein the pharmacologically active agent is pindolol.

5. The method of claim 1, wherein the pharmacologically active agent and the enhancer are present in a single pharmaceutical composition, and wherein the composition further includes a pharmaceutically acceptable inert vehicle.

6. A method for enhancing the rate of penetration of a pharmacologically active agent through the skin, comprising applying to a selected area of intact skin: (a) a therapeutically effective amount of the pharmacologically active agent; and (b) a permeation enhancer consisting essentially of a sorbitan ester having the structural formula

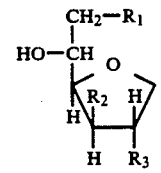

wherein $R_1$ has the formula —O(CO)R', R' is selected from the group consisting of saturated, mono-unsaturated, di-unsaturated, or tri-unsaturated aliphatic hydrocarbon substituents of 7 to 21 carbon atoms optionally containing 1 to 3 hydroxyl groups, and $R_2$ and $R_3$ are independently selected from the group consisting of hydroxyl and—O(CO)R', and a $C_1$-$C_4$ aliphatic alcohol.

7. The method of claim 1 wherein R' is selected from the group consisting of saturated, mono-unsaturated, di-unsaturated, or tri-unsaturated aliphatic hydrocarbon substituents of 11-21 carbon atoms optionally containing 1-3 hydroxyl groups, and $R_2$ and $R_3$ are both hydroxyl.

8. The method of claim 7 wherein the sorbitan ester is selected from the group consisting of sorbitan monooleate, sorbitan monolaurate, and mixtures thereof.

9. The method of claim 6 wherein the $c_1$-$C_4$ aliphatic alcohol is selected from the group consisting of ethanol, n-propanol, isopropanol, t-butanol, and mixtures thereof.

10. The method of claim 6, wherein the pharmacologically active agent and the enhancer are present in a single pharmaceutical composition, and wherein the composition further includes a pharmaceutically acceptable inert vehicle.

11. A composition of matter for the transdermal administration of a pharmaceutically active agent, comprising: (a) a therapeutically effective amount of the pharmacologically active agent; and (b) a permeation enhancer consisting essentially of a sorbitan ester having the structural formula

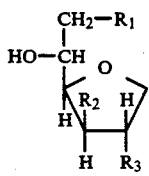

wherein $R_1$ has the formula —O(CO)R', R' is selected from the group consisting of saturated, mono-unsaturated, di-unsaturated, or tri-unsaturated aliphatic hydrocarbon substitutuents of 7 to 21 carbon atoms optionally containing 1 to 3 hydroxyl groups, and $R_2$ and $R_3$ are independently selected from the group consisting of hydroxyl and —O(CO)R'.

12. The composition of claim 11 wherein the sorbitan ester has the structural formula

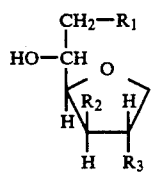

wherein $R_1$ has the formula —O(CO)R', where R' is selected from the group consisting of saturated, mono-unsaturated, di-unsaturated, or tri-unsaturated aliphatic hydrocarbon substituents of 7 to 21 carbon atoms optionally containing 1 to 3 hydroxyl groups, and $R_2$ and $R_3$ are independently selected from the group consisting of hydroxyl and —O(CO)R'.

13. The composition of claim 12 wherein R' is selected from the group consisting of saturated, mono-unsaturated, di-unsaturated, or tri-unsaturated aliphatic hydrocarbon substituents of 11-21 carbon atoms optionally containing 1-3 hydroxyl groups, and $R_2$ and $R_3$ are both hydroxyl.

14. The composition of claim 13 wherein the sorbitan ester is selected from the group consisting of sorbitan monooleate, sorbitan monolaurate, and mixtures thereof.

15. The composition of claim 11 wherein the pharmacologically active agent is pindolol.

16. The composition of claim 11 further including a pharmaceutically acceptable inert vehicle.

17. A composition of matter for the transdermal administration of a pharmacologically active agent comprising: (a) a therapeutically effective amount of the pharmacologically active agent; and (b) a permeation enhancer consisting essentially of a sorbitan ester having the structural formula

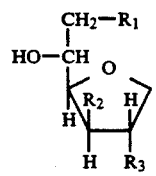

wherein $R_1$ has the formula —O(CO)R', R' is selected from the group consisting of saturated, mono-unsaturated, di-unsaturated, or tri-unsaturated aliphatic hydrocarbon substituents of 7 t 21 carbon atoms optionally containing 1 to 3 hydroxyl groups, and $R_2$ and R are independently selected from the group consisting of hydroxyl and —O(CO)R', and a $C_1$-$C_4$ aliphatic alcohol.

18. The composition of claim 17 wherein R' is selected from the group consisting of saturated, mono-unsaturated, di-unsaturated, or tri-unsaturated aliphatic hydrocarbon substituents of 11-21 carbon atoms optionally containing 1-3 hydroxyl groups, and $R_2$ and $R_3$ are both hydroxyl.

19. The composition of claim 18 wherein the sorbitan ester is selected from the group consisting of sorbitan monooleate, sorbitan monolaurate, and mixtures thereof.

20. The composition of claim 17 wherein the $C_1$-$C_4$ aliphatic alcohol is selected from the group consisting of ethanol, n-propanol, isopropanol, t-butanol, and mixtures thereof.

21. The composition of claim 17 wherein the pharmacologically active agent is pindolol.

* * * * *